United States Patent
Le Peltier et al.

(10) Patent No.: US 6,187,985 B1
(45) Date of Patent: *Feb. 13, 2001

(54) PROCESS FOR DEHYDROGENATING SATURATED ALIPHATIC HYDROCARBONS TO OLEFINIC HYDROCARBONS

(75) Inventors: Fabienne Le Peltier; Blaise Didillon, both of Rueil Malmaison; Olivier Clause, Chatou, all of (FR)

(73) Assignee: Institut Francais du Petrole, Rueil Malmaison Cedex (FR)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/182,660

(22) Filed: Oct. 30, 1998

(30) Foreign Application Priority Data

Oct. 31, 1997 (FR) .................................................. 97 13685

(51) Int. Cl.[7] .................. C07C 2/02; C07C 5/09; C07C 5/333

(52) U.S. Cl. .................. 585/661; 585/442; 585/443; 585/444; 585/660; 585/629; 585/627

(58) Field of Search .................. 585/442, 443, 585/444, 660, 661, 627, 629

(56) References Cited

U.S. PATENT DOCUMENTS

| | | | | |
|---|---|---|---|---|
| 2,426,604 | * | 9/1947 | Ferel | 585/259 |
| 3,200,167 | * | 8/1965 | Reich | 585/260 |
| 3,297,776 | | 1/1967 | Reich et al. | 585/262 |
| 3,669,875 | * | 6/1972 | Plank et la. | 208/65 |
| 3,830,726 | * | 8/1974 | Weissang et al. | 208/138 |
| 3,929,683 | * | 12/1975 | Antos | 208/138 |
| 3,992,468 | * | 11/1976 | Cosyns et al. | 585/489 |
| 4,409,410 | * | 10/1983 | Cosyns et al. | 585/259 |
| 4,507,401 | * | 3/1985 | Dubois et al. | 502/242 |
| 4,513,098 | * | 4/1985 | Tsao | 502/216 |
| 4,548,918 | * | 10/1985 | Bournonville et al. | 502/154 |
| 4,645,752 | * | 2/1987 | Defresne et al. | 502/66 |
| 4,658,080 | * | 4/1987 | McFarland | 585/260 |
| 4,691,070 | * | 9/1987 | Nakamura et al. | 585/259 |
| 4,727,216 | | 2/1988 | Miller | 585/660 |
| 4,737,262 | * | 4/1988 | Franck et al. | 208/65 |
| 5,417,844 | * | 5/1995 | Boitaux | 585/260 |
| 5,456,822 | * | 10/1995 | Marcilly et al. | 206/136 |
| 5,510,550 | * | 4/1996 | Cheung et al. | 585/259 |
| 5,679,241 | * | 10/1997 | Stanley | 585/262 |
| 5,679,841 | * | 10/1997 | Stanley | 585/262 |
| 5,877,369 | | 3/1999 | Wu et al. | 585/419 |

FOREIGN PATENT DOCUMENTS

| | | | |
|---|---|---|---|
| 0 623 384 | * | 11/1994 | (EP) . |
| 0 623 385 | * | 11/1994 | (EP) . |
| 2 495 605 | * | 6/1982 | (FR) . |
| 2 594 711 | * | 8/1987 | (FR) . |
| 2 653 118 | * | 4/1991 | (FR) . |
| 2 671 347 | * | 7/1992 | (FR) . |
| 2 694 286 | * | 2/1994 | (FR) . |

\* cited by examiner

*Primary Examiner*—Walter D. Griffin
*Assistant Examiner*—Tam M. Nguyen
(74) *Attorney, Agent, or Firm*—Millen, White, Zelano & Branigan, P.C.

(57) ABSTRACT

A process for dehydrogenating $C_5$–$C_{22}$ aliphatic hydrocarbons to the corresponding olefinic hydrocarbons is carried out in the presence of a catalyst comprising at least one support, at least one metal from group VIII of the periodic table and at least one additional element M selected from the group formed by germanium, tin, lead, rhenium, gallium, indium, and thallium. The process is characterized in that the catalyst is prepared using a process in which said metal M is introduced in an aqueous solvent in the form of at least one organometallic compound comprising at least one carbon-M bond.

31 Claims, No Drawings

PROCESS FOR DEHYDROGENATING SATURATED ALIPHATIC HYDROCARBONS TO OLEFINIC HYDROCARBONS

FIELD OF THE INVENTION

The present invention relates to a novel process for dehydrogenating $C_5$–$C_{22}$ aliphatic hydrocarbons to the corresponding olefinic hydrocarbons in the presence of a catalyst comprising at least one support, at least one metal from group VIII of the periodic table, and at least one additional element M selected from germanium, tin, lead, rhenium, gallium, indium and thallium. The catalyst can also contain a further metal selected from the group formed by alkali or alkaline-earth metals and/or a metalloid such as sulphur and/or any other chemical element such as a halogen or a halogen-containing compound.

BACKGROUND OF THE INVENTION

Catalyst formulations used in hydrocarbon conversion processes have been the subject of a very large number of studies. Patents and publications demonstrating that the addition of promoters to a base metal improves the quality of catalysts exist in large numbers. For paraffin dehydrogenation catalysts, catalysts comprising, in addition to a support, a noble metal from the platinum family and at least one additional metal M (United States patents U.S. Pat. No. 3,998,900 and U.S. Pat. No. 3,531,543) have been known for a long period. The acidity of the refractory inorganic support can lead to undesirable secondary reactions such as cracking and isomerisation. For this reason the oxide support is generally neutralised by adding at least one alkali or alkaline-earth element.

The metal phase is the hydro-dehydrogenating function which dehydrogenates the paraffins and hydrogenates coke precursors. However, platinum has a hydrogenolysing activity which deleteriously affects the yields of the desired olefins in the paraffin dehydrogenation process. This hydrogenolysing activity can be substantially reduced, and thus the selectivity of the catalyst can be increased, by adding an additional metal M. Further, adding this element M can also increase the hydrogenating properties of the platinum, encouraging hydrogenation of the coke precursors and thus increasing the stability of the catalyst.

Such elements are added in different forms such as mineral salts or organometallic compounds. The manner in which such modifying agents are introduced is not unimportant as it dictates the properties of the catalyst to a great extent. Thus a metal M is advantageously introduced using an organometallic compound of that metal M. Such a technique for introducing a metal M has been described in U.S. Pat. No. 3,531,543. Metal M is introduced in the form of at least one organometallic compound selected from the group formed by complexes, in particular carbonyl or polyketone complexes of metals M, and metal hydrocarbyls of metal M such as alkyls, cycloalkyls, aryls, metal alkylaryls and metal arylalkyls.

Introducing the additional element M in the form of an organometallic compound leads to more effective catalysts but necessitates the use of an organic solvent. The impregnating solvent described in United States patent U.S. Pat. No. 4,548,918 is selected from the group formed by oxygen-containing organic solvents containing 2 to 8 carbon atoms per molecule, paraffin, naphthene or aromatic hydrocarbons essentially containing 6 to 15 carbon atoms per molecule, and halogen-containing oxygen-containing organic compounds containing I to 15 carbon atoms per molecule. Such solvents can be used alone or mixed together.

SUMMARY OF THE INVENTION

In the present invention we have discovered that particularly effective catalysts can be prepared by introducing metal M in the form of an organometallic complex which is soluble in an aqueous solvent. This represents a considerable advance as regards ease of use during production of the catalyst. Using industrial quantities of organic solvents has many disadvantages as regards safety (flammability, toxicity) and as regards costs.

The support for the catalyst of the invention comprises at least one refractory oxide which is generally selected from oxides of metals from groups IIA, IIIA, IIIB, IVA or IVB of the periodic table such as oxides of magnesium, aluminium, silicon, titanium, zirconium or thorium, used alone or mixed together or mixed with oxides of other elements from the periodic table. Charcoal can also be used. X, Y, mordenite, faujasite, ZSM-5, ZSM-4 or ZSM-8 type zeolites or molecular sieves can also be used, as well as mixtures of oxides of group IIA, IIIA, IIIB, IVA or IVB metals with a zeolitic material.

Alumina constitutes the preferred support, the specific surface area of which is advantageously in the range 5 to 400 $m^2$ per gram, preferably in the range 50 to 350 $m^2$ per gram.

In addition to a support, the catalyst of the invention includes:

a) at least one group VIII metal selected from iridium, nickel, palladium, platinum, rhodium and ruthenium. Platinum and palladium are preferred metals. The percentage by weight is in the range 0.1% to 10%, preferably in the range 0.1% to 5%.

b) at least one additional element M selected from the group formed by germanium, tin, lead, rhenium, gallium, indium and thallium. Tin and germanium are preferred elements. The percentage by weight is in the range 0.01% to 10%, preferably in the range 0.02% to 5%. In some cases, at least two of the metals from this group can advantageously be used at once.

c) preferably, 0.1% to 3% by weight of at least one alkali or alkaline-earth metal.

Depending on the application, the catalyst can also contain 0.01% to 3% by weight of a halogen or halogen-containing compound. It can also contain 0.01% to 2% by weight of an element such as sulphur.

The catalyst can be prepared using different procedures for impregnating the support and the invention is not limited to any specific impregnation procedure. When several solutions are used, intermediate drying and/or calcining steps can be carried out.

The additional element M can be introduced during production of the support. One method, for example, consists of blending the moist powdered support with catalyst precursors and then forming and drying.

The group VIII metal, additional metal M, alkali or alkaline-earth metal, optional halogen or halogen-containing compound, and optional metalloid, can be introduced simultaneously or successively, in any order. In accordance with the invention, the characteristic feature of contact with the organometallic element M is that it is introduced in an aqueous solvent.

In a further method, the additional metal M can be introduced during synthesis of the support using a sol-gel type technique. As an example, for a support containing alumina, a mixed metal M—alumina gel can be obtained by hydrolysing an organic solution of $Al(OR')_3$ in a solvent such as ROH or R'OH with an aqueous solution of an organometallic compound of metal M. R and R' represent a methyl, ethyl, isopropyl, n-propyl or butyl type alkyl group or a heavier group such as n-hexyl. The alcoholic solvent must be highly dehydrated before introducing the aluminium alcoholate. After hydrolysis, heat treatment of the gel obtained carried out at a temperature in the range 200° C. to 800° C., preferably in the range 300° C. to 700° C., and more preferably in the range 400° C. to 500° C., ensures complete reaction of the hydrosoluble organometallic compound of metal M with the gel, which involves the formation of the mixed oxide $Al_2O_3$—$MO_x$.

In a still further method, metal M can be added to an alumina sol. U.S. Pat. No. 3,929,683 describes introducing tin in the form of a salt, for example $SnCl_2$ into an alumina sol. In the present invention, it is possible to add a hydrosoluble organometallic compound of metal M to an alumina hydrosol, obtained, for example, by precipitating an acid solution of $AlCl_3$ at pH 4–5, then encouraging the compound of metal M to react with the alumina hydrosol for example using heat or a base.

The precursor of element M can be selected from the group formed by halogen-containing compounds, hydroxides, oxides, carbonates and carboxylates of organometallic compounds of element M. These compounds comprise at least one carbon-M bond. The precursor of element M can also be selected from compounds with general formula $(R_1)_xM(R_2)_y$ where x+y=the valency of metal M and where $R_1$ is selected from the group formed by alkyl, cycloalkyl, aryl, alkylaryl and arylalkyl functions, and $R_2$ is a function with formula $C_aH_bR'_c$, where R' represents a hydroxide, carboxylate, $PO_3H$ or $SO_3H$ function.

In one preparation technique in accordance with the invention, the catalyst is obtained by impregnating the support using an aqueous or organic solution of at least one alkali or alkaline-earth metal, the volume of the solution preferably being equal to the retention volume of the support, or in excess with respect to that volume. The impregnated support is then filtered, dried and calcined in air, normally between 110° C. and about 550° C. At least one group VIII metal compound is then introduced using an aqueous or organic solution. the volume of the solution preferably being in excess with respect to the retention volume of the support or equal to that volume. The impregnated support is then filtered. dried and calcined in air, normally between 110° C. and about 550° C., then reduced in hydrogen at a temperature which is normally in the range about 200° C. to about 600° C., preferably in the range about 300° C. to about 500° C. The product obtained is then impregnated with an aqueous solution of a compound of tin, germanium, lead, rhenium, gallium, indium or thallium. Particularly advantageously, an aqueous solution of a carboxylate compound of tin is used, for example tributyl tin acetate.

The volume of the aqueous solution is preferably equal to the retention volume of the support, more preferably in excess with respect to that volume. The concentration of at least one metal M in the aqueous solution is advantageously in the range 0.01 to 25 mmol/l, preferably in the range 0.5 to 20 mmol/l, and more preferably in the range 0.5 to 15 mmol/l. The pH of the solution is advantageously between 10 and 14, preferably between 10 and 12.

After leaving the support impregnated with the group VIII metal in contact with the solution containing at least one compound of element M for several hours, the product is filtered, optionally washed with water, then dried. In this method, the operation is completed by reducing between 300° C. and 600° C., preferably in a stream of hydrogen for several hours.

In a further technique in accordance with the invention, the catalyst is obtained by impregnating with an aqueous solution of at least one compound of said metal M, the volume of the solution preferably being equal to the retention volume of the support, more preferably in excess with respect to that volume. Particularly advantageously, an aqueous solution of a tin carboxylate compound is used. The concentration of at least one metal M in the aqueous solution is advantageously in the range 0.01 to 25 mmol/l, preferably in the range 0.5 to 20 mmol/l, more preferably in the range 0.5 to 15 mmol/l. The pH of the solution is advantageously in the range 10 to 14, more preferably in the range 10 to 12. After leaving the solid and impregnating solution in contact for several hours, the product is then dried. The operation is normally completed by calcining between 300° C. and 600° C., preferably in a stream of air for several hours. The solid obtained can then be impregnated using an aqueous or organic solution of at least one alkali or alkaline-earth compound, the volume of the solution preferably being equal to the retention volume of the support or in excess with respect to that volume. The impregnated support is then dried and calcined in air, normally between 110° C. and about 550° C. In addition and advantageously, at least one compound of said element M and at least one alkali or alkaline-earth element can be introduced by impregnating the support with a common aqueous solution, the volume of the solution preferably being equal to the retention volume of the support or in excess with respect to that volume. After leaving the solid in contact with the impregnating solution for several hours, the product is then dried. The operation is normally completed by calcining between 300° C. and 600° C., preferably in a stream of air for several hours. The solid obtained is then impregnated using an aqueous or organic solution of at least one group VIII metal compound, the volume of the solution preferably being in excess with respect to the retention volume of the support or equal to that volume. After several hours of contact, the product obtained is dried and calcined in air between 300° C. and 600° C., preferably in a stream of air for several hours.

Before use, the catalyst is reduced in hydrogen, for example between 20° C. and 600° C., to obtain an active metal phase. This treatment consists, for example, in slowly raising the temperature in a stream of hydrogen to the maximum reduction temperature, in the range 20° C. to 600° C., for example, preferably in the range 90° C. to 500° C., followed by maintaining that temperature for a period of 1 to 6 hours, for example.

This reduction can be carried out immediately after calcining or later at the user's location. It is also possible to directly reduce the dried product at the user's location.

It is also possible to carry out prior reduction of the group VIII metal compound in solution using organic molecules with a reducing nature such as formic acid. The compound of additional element M can be introduced simultaneously or successively. One possibility consists of filtering then drying the catalyst obtained. It can then be calcined followed by reduction using the conditions described above. It is also possible to carry out direct reduction of the dried product.

In accordance with the invention, the catalyst described above is used in processes for dehydrogenating $C_5$–$C_{22}$ paraffins. Processes for dehydrogenating light $C_5$ paraffins can be used to upgrade aliphatic hydrocarbons with a low boiling point such as pentanes and isopentanes which are to be recovered after extracting unsaturated compounds from $C_5$ steam cracking or catalytic cracking cuts. Processes for dehydrogenating longer paraffins are important commercial processes due to the fact that mono-olefins are currently in great demand for preparing biodegradable detergents or pharmaceutical products, for example.

These different processes are differentiated by their choice of operating conditions and the composition of the feed. The operating conditions are adjusted depending on the feed to be treated, in known manner so as to obtain the best pressure-temperature-yield and activity match. The dehydrogenation reaction is generally carried out at a pressure in the range 0.2 to 20 bars absolute preferably at a pressure of 1 to 10 bars absolute and at a temperature in the range 400° C. to 800° C. depending on the nature of the feed.

The temperature is advantageously in the range 400° C. to 550° C. for a feed essentially comprising isopentane. The temperature is advantageously in the range 450° C. to 550° C. for a feed comprising mainly paraffins containing 9 to 22 carbon atoms per molecule. The feed can also contain unsaturated hydrocarbons containing 5 to 22 carbon atoms per molecule. The mass flow rate of the treated feed per unit mass of catalyst is generally in the range 0.5 to 100 kg/kg/h. It can advantageously use hydrogen as a diluent. The hydrogen/hydrocarbon molar ratio is generally in the range 0 to 20, preferably in the range 0 to 6.

The following examples illustrate the invention without in any way limiting its scope.

EXAMPLE 1

Two catalysts A and B were prepared, comprising 0.3% by weight of platinum. 0.8% by weight of tin and 0.7% by weight of lithium. The support was a alumina with a specific surface area of 210 m² per gram.

Catalyst A (comparative)

Catalyst A was prepared using prior art techniques. 60 cm³ of an aqueous solution of lithium acetate containing 0.7 g of lithium was added to 100 g of alumina support. It was left in contact for 3 hours then the solid was dried for I hour at 120° C. and calcined at 350° C. for 2 hours. The solid was then brought into contact with 60 cm³ of an aqueous tin acetate solution containing 0.8 g of tin. After 3 hours contact, the solid was dried for 1 hour at 120° C. and calcined for 2 hours at 530° C. Platinum was then introduced by adding 400 cm³ of a toluene solution containing 0.3 g of platinum in the form of platinum acetylacetonate. It was left in contact for 24 hours then dried for I hour at 120° C. and calcined for 2 hours at 530° C.

Catalyst B (in accordance with the invention)

60 cm of an aqueous solution of lithium acetate containing 0.7 g of lithium was added to 100 g of an alumina support. It was left in contact for 3 hours then the solid was dried for 1 hour at 120° C. and calcined at 350° C. for 2 hours. Platinum was introduced directly by adding 400 cm³ of a toluene solution containing 0.3 g of platinum in the, form of platinum acetylacetonate. It was left in contact for 24 hours then filtered, dried for 1 hour at 120° C. and calcined for 2 hours at 530° C. The solid was then reduced in hydrogen at 450° C. and introduced into a reactor containing 400 cm³ of an aqueous ammoniacal solution (pH 10) containing 0.8 g of tin in the form of tributyltin acetate ($Bu_3SnOC(O)CH_3$) without allowing more air to enter. After 24 hours of contact, the reaction mixture was filtered, washed, dried and reduced at 450° C.

EXAMPLE 2

Catalysts A and B underwent an n-dodecane dehydrogenation test carried out in an isothermal tube reactor. 2 g of catalyst was reduced at 450° C. for 2 hours in a stream of 4 liters per hour of hydrogen. The operating conditions were as follows:

- feed: n-dodecane
- temperature: 450° C. or 470° C.
- pressure: 0.2 MPa
- $H_2/nC_{12}$ (molar): 5
- mass flow rate of liquid $nC_{12}$/mass of catalyst: 80 h$^{-1}$ The results obtained under these conditions are shown in Table 1. The $nC_{12}$ conversion values and the yields are expressed as % by weight with respect to the feed.

TABLE 1

| Catalysts | Temperature (° C.) | $nC_{12}$ Conversion (%) | Yields (%) | |
|---|---|---|---|---|
| | | | $nC_{12}$ olefins | aromatics |
| A | 450 | 10.4 | 9.6 | 0.3 |
| | 470 | 12.1 | 10.3 | 0.8 |
| | 450 | 6.0 | 5.6 | 0.1 |
| B | 450 | 10.6 | 9.7 | 0.2 |
| | 470 | 15.0 | 13.2 | 0.6 |
| | 450 | 9.6 | 8.4 | 0.2 |

Catalyst B, prepared in accordance with the invention in an aqueous medium from an organometallic Sn precursor, had higher olefin yields than those of catalyst A prepared in an aqueous phase from a mineral Sn compound. Further, as the catalytic results corresponding to the "turning point" at 450° C. indicate, catalyst B is more stable than catalyst A.

What is claimed is:

1. A process comprising:
   preparing a catalyst comprising at least one support, at least one metal from group VIII of the periodic table and at least one additional element M selected from the group consisting of germanium, tin, lead, rhenium, gallium, indium, gold, silver and thallium, wherein said additional element M is in the form of at least one water-soluble organometallic compound containing at least one carbon-M bond, the preparation of said catalyst comprising introducing an aqueous solution of said organometallic compound, and
   contacting said catalyst in a dried, calcined and reduced form with an aliphatic hydrocarbon feed, in the presence of hydrogen so as to dehydrogenate the aliphatic hydrocarbon to form the corresponding olefin.

2. A process for dehydrogenating aliphatic hydrocarbons to the corresponding olefinic hydrocarbons according to claim 1, characterized in that the feed is constituted by $C_5$–$C_{22}$ aliphatic hydrocarbons.

3. A process according to claim 1, in which the catalyst further contains at least one alkali or alkaline-earth metal.

4. A processing according to claim 1, in which the catalyst further contains sulfur.

5. A process according to claim to 1, in which the catalyst further contains at least one halogen or halogen-containing compound.

6. A process according to claim 1 in which in the catalyst, the croup VIII metal is iridium, nickel, palladium, platinum, rhodium or ruthenium.

7. A process according to claim 1 in which in the catalyst, element M is germanium and tin.

8. A process according to claim 1 in which in the catalyst, a precursor of element M is selected from the group consisting of hydroxides, halogen-containing compounds, and carboxylates of organic compounds of element M, compounds with general formula $(R_1)_x M(R_2)_y$ where x+y=the valency of metal M and where $R_1$ is selected from the group formed by alkyl, cycloalkyl, aryl, alkylaryl and arylalkyl functions, and $R_2$ is a function with formula $C_a H_b R'_c$, where R' represents a hydroxide, carboxylate, $PO_3H$ or $SO_3H$ function.

9. A process according to claim 8 in which the catalyst, the precursor of element M is a carboxylate of an organic compound of element M.

10. A process according to claim 9 in which in the catalyst, the precursor of element M is tributyltin acetate.

11. A process according to claim 1, in which during preparation of the catalyst, the group VIII metal, additional element M, alkali or alkaline-earth metal, optional halogen and optional metalloid are introduced into the support successively or simultaneously.

12. A process according to claim 1, in which the catalyst is prepared by carrying out the following steps in any order:
    impregnating using an aqueous or organic solution of at least one group VIII metal, filtering, drying, calcining and reducing;
    impregnating using an aqueous solution of at least one compound of additional element M, filtering, drying, optionally reducing them calcining.

13. A process according to claim 1, in which during preparation of the catalyst, the support is impregnated with an aqueous solution of at least one metal M, the volume of the solution being at least equal to the retention volume of the support.

14. A process according to claim 1, in which during preparation of the catalyst, the concentration of at least one metal M in the aqueous solvent is in the range 0.01 to 25 mmol/l.

15. A process according to claim 14, in which the concentration of at least one metal M in the aqueous solvent is in the range 0.5 to 20 mmol/l.

16. A process according to claim 1, in which during preparation of the catalyst, the pH of the aqueous solution of at least one compound of metal M is selected so as to be between 10 and 14.

17. A process according to claim 1, in which during preparation of the catalyst, additional element M is introduced during production of the support.

18. A process according to claim 17, in which during preparation of the catalyst, the additional element M is introduced during synthesis of the support using a sol-gel type technique.

19. A process according to claim 18, in which during preparation of the catalyst, an aqueous solution of an organometallic compound of metal M is used to hydrolyse an organic solution of an alkoxy compound of a metal of the support in an alcoholic solvent, and heated to a temperature in the range 200° C. to 800° C.

20. A process according to claim 1, in which the catalyst is reduced in hydrogen at a temperature in the range 20° C. to 600° C.

21. A process according to claim 19, in which prior reduction of the group VIII metal compound is carried out in solution by organic molecules with a reducing nature such as formic acid.

22. A process according to claim 1, in which the feed to be treated is brought into contact with the catalyst at a pressure in the range 0.2 to 20 bars absolute and at a temperature in the range 400° C. to 800° C., with a mass flow rate of treated feed per unit mass of catalyst in the range 0.5 to 100 kg/kg/hour.

23. A process according to claim 1, in which the temperature is in the range 400° C. to 550° C. for a feed comprising isopentane.

24. A process according to claim 1, in which the temperature is in the range 450° C. to 550° C. for a feed containing 9 to 22 carbon atoms.

25. A process according to claim 1, in which hydrogen is used to dilute the hydrocarbons, the hydrogen/hydrocarbon molar ratio being in the range 0 to 20.

26. A process according to claim 1, wherein said support is selected from the group consisting of oxide of a group IIA metal, an oxide of a group IIIA metal, an oxide of a group IIIB metal, an oxide of a group IVA metal, an oxide of a group IVB metal, charcoal, x, y, mordenite, faujasite, ZSM-5, ZSM-4, ZSM-8 and mixtures thereof.

27. A process according to claim 1, wherein the support is an oxide of magnesium, aluminum, silicon, titanium, zirconium, or thorium.

28. A process according to claim 1, wherein the supprot is alumina.

29. A process according to claim 1, wherein said catalyst consist essentially of said at least one support, said at least one metal from group VIII of the periodic table, and said at least one additional element M.

30. A process to claim 1, wherein said catalyst consist of said at least one support, said at least one metal from group VIII of the periodic table, and said at least one additional element M.

31. A process according to claim 28, wherein said catalyst consist essentially of said at least one support, said at least one metal from group VIII of the periodic table, and said at least one additional element M.

* * * * *

UNITED STATES PATENT AND TRADEMARK OFFICE
CERTIFICATE OF CORRECTION

PATENT NO.    : 6,187,985 B1
DATED         : February 13, 2001
INVENTOR(S)   : Le Peltier et al.

It is certified that error appears in the above-identified patent and that said Letters Patent is hereby corrected as shown below:

Column 6,
Line 62, change "croup" to -- group --.
Line 65, change "and" to -- or --.

Signed and Sealed this

Thirteenth Day of May, 2003

JAMES E. ROGAN
*Director of the United States Patent and Trademark Office*